(12) United States Patent
Hall

(10) Patent No.: US 9,931,184 B2
(45) Date of Patent: Apr. 3, 2018

(54) ARRANGEMENT WITH AN IMPLANT AND/OR A UNIT BELONGING TO SAID IMPLANT, AND METHOD FOR PRODUCTION OF THE IMPLANT AND/OR UNIT

(71) Applicant: NOBEL BIOCARE SERVICES AG, Glattbrugg (CH)

(72) Inventor: Jan Hall, Gothenburg (SE)

(73) Assignee: Nobel Biocare Services AG, Kloten (CH)

( * ) Notice: Subject to any disclaimer, the term of this patent is extended or adjusted under 35 U.S.C. 154(b) by 578 days.

(21) Appl. No.: 14/109,452

(22) Filed: Dec. 17, 2013

(65) Prior Publication Data

US 2014/0174939 A1 Jun. 26, 2014

Related U.S. Application Data

(62) Division of application No. 10/582,468, filed as application No. PCT/SE2004/001806 on Dec. 6, 2004.

(30) Foreign Application Priority Data

Dec. 11, 2003 (SE) ..................................... 0303323

(51) Int. Cl.
*C25D 9/00* (2006.01)
*C25D 11/26* (2006.01)
(Continued)

(52) U.S. Cl.
CPC ........ *A61C 13/0012* (2013.01); *A61C 8/0012* (2013.01); *A61C 8/0013* (2013.01);
(Continued)

(58) Field of Classification Search
CPC .... C25D 11/26; A31C 13/0012; A61K 6/0235
(Continued)

(56) References Cited

U.S. PATENT DOCUMENTS

| | | |
|---|---|---|
| 4,261,063 A | 4/1981 | Blanquaert |
| 5,152,794 A | 10/1992 | Davidson |

(Continued)

FOREIGN PATENT DOCUMENTS

| | | | |
|---|---|---|---|
| CH | 2442582 A1 * | 10/2002 | ......... A61F 2/30767 |
| DE | 3445848 | 6/1986 | |

(Continued)

OTHER PUBLICATIONS

International Search Report for Application No. PCT/SE2004/001806 (the PCT counterpart of the parent application) dated Apr. 6, 2005.

(Continued)

*Primary Examiner* — Brian W Cohen
(74) *Attorney, Agent, or Firm* — Knobbe, Martens, Olson & Bear LLP

(57) ABSTRACT

An implant (5, 13) and/or a unit (9), e.g. spacer sleeve, belonging to said implant is/are intended to extend through a hole (4') formed in a jaw bone (2) and through soft tissue (3) belonging to the jaw bone and to comprise one or more outer layers of principally titanium dioxide. Each layer consists of crystalline titanium dioxide which largely or completely assumes the anatase phase. The invention also relates to a method for production of such a dental implant (5, 13) and/or of a unit (9) belonging to it, which has one or more outer layers of titanium dioxide. The method is an anodic oxidation method in which the part or parts bearing the outer layer(s) is/are applied to electrolyte under voltage, e.g. comprising sulfuric acid and phosphoric acid, and the voltage (U) and the dwell time of the part or parts in the (Continued)

electrolyte are chosen such that titanium dioxide, largely or completely assuming the crystalline anatase phase, is formed. Excellent bone guidance and soft tissue integration can be achieved in this way.

14 Claims, 2 Drawing Sheets

(51) Int. Cl.
C25D 11/02 (2006.01)
A61C 13/00 (2006.01)
A61C 8/00 (2006.01)
A61L 27/06 (2006.01)
A61L 27/50 (2006.01)
A61K 6/02 (2006.01)

(52) U.S. Cl.
CPC .......... *A61C 8/0015* (2013.01); *A61K 6/0235* (2013.01); *A61L 27/06* (2013.01); *A61L 27/50* (2013.01); *C25D 11/022* (2013.01); *C25D 11/26* (2013.01)

(58) Field of Classification Search
USPC .................................. 205/322, 333, 212
See application file for complete search history.

(56) References Cited

U.S. PATENT DOCUMENTS

| | | | |
|---|---|---|---|
| 5,180,394 A | | 1/1993 | Davidson |
| 5,354,390 A | * | 10/1994 | Haszmann ........... A61C 8/0015 128/898 |
| 5,697,779 A | | 12/1997 | Sachdeva et al. |
| 6,103,363 A | | 8/2000 | Boire et al. |
| 6,174,167 B1 | | 1/2001 | Wohrle |
| 6,183,255 B1 | | 2/2001 | Oshida |
| 6,527,554 B2 | | 3/2003 | Hurson et al. |
| 6,951,463 B2 | | 10/2005 | Masuhara et al. |
| 2001/0002994 A1 | | 6/2001 | Masuhara et al. |
| 2005/0019365 A1 | | 1/2005 | Frauchiger et al. |
| 2005/0103639 A1 | * | 5/2005 | Lu .................... C25D 11/26 205/322 |
| 2005/0113834 A1 | * | 5/2005 | Breitenstien ............ A61L 27/04 606/331 |
| 2005/0175658 A1 | | 8/2005 | DiMauro et al. |
| 2006/0229715 A1 | | 10/2006 | Istephanous et al. |
| 2007/0275350 A1 | | 11/2007 | Hall |
| 2008/0097618 A1 | | 4/2008 | Baker et al. |

FOREIGN PATENT DOCUMENTS

| | | |
|---|---|---|
| DE | 4311772 | 10/1993 |
| DE | 4216122 | 11/1993 |
| JP | 11-033106 | 2/1999 |
| JP | 2000-116673 | 4/2000 |
| JP | 2002-102330 | 4/2002 |
| SE | 514202 | 1/2001 |
| WO | WO 00/72776 | 12/2000 |
| WO | WO 00/72777 | 12/2000 |
| WO | WO 01/76653 | 10/2001 |
| WO | WO 02/078759 | 10/2002 |
| WO | WO 02/096475 | 12/2002 |
| WO | WO 03/003937 | 1/2003 |
| WO | WO 03/063925 | 8/2003 |
| WO | WO 2004/091424 | 10/2004 |
| WO | WO 2005/055858 | 6/2005 |
| WO | WO 2005/055859 | 6/2005 |

OTHER PUBLICATIONS

Hanaor et al. "Review of the Anatase to Rutile Phase Transformation". Journal of Material Science, 2011, vol. 46, pp. 855-874.
Ausger Electron Spectroscopic Studies of Titanium Implants Treated by Several Finishing Porcedures, J. Showa Univ. Dent. soc. 11:322-326 1991.
Born, R., et al. "Surface analysis of titanium based biomaterials", J. Anal. Chem. (1998) 361:697-700, in 4 pages.
Ignatov, V. "Biocompartible Coatings on Titanium Implants" Science and Technology, 2003, Publication date: Jun. 28, 2003, pp. 197-201 in 5 pages.
Kokubo, T., et al. "Novel bioactive materials with different mechanical properties" Jun. 2003, vol. 24, No. 13; pp. 2-16 in 15 pages.
D2c Katalog "TiUnite—Die einzgartige Titanoxidoberflache, jetz neu im Branemark-System", Seite 3, Zeilen 11 und 12,; Seite 2, Zeilen 7 bis 13.
D2f Katalog "Replace—TiUnite, a Unique Oxidized Titanium Surface" Seite 2, Zeilen 1 bis 5.
D7 Publikation G.A. Battiston, et al. "Dental Implants of Complex Form Coated by Nanostructured TiO2 Thin Films via MOCVD" Materials Science Forum vol. 352 (2000) Seiten 151-158 "abstract"; Seite 135, Zeilen 1 bis 9.
Del Corto, B., et al., "Decreased bacterial adhesion to surface-treated titanium", The International Journal of Artificial Organs, vol. 28, No. 7, 2005, pp. 718-730.
D17—Response to USPTO (Remarks in Amendment for present Application) dated Dec. 27, 2011 in 4 pages.
D18—Reply from USPTO (Office Action of present Application) dated Jan. 31, 2012 in 8 pages.
D20—Ruano, Rogerio, et al., Effect of a Ceramic and a Non-Ceramic Hydroxyapatite on Cell Growth and Procollagen Synthesis of Cultured Human Gingival Fibroblasts, J. Periodontol., Apr. 2000, vol. 71, No. 4, pp. 540-545.
D21—Expressing Universality, dated Sep. 8, 2012 in 8 pages.
Grounds for the Decision in related application No. EP 04820332.7, dated Feb. 1, 2015 in 43 pages.
Summons to Oral Proceeding and Annex in related application No. EP 04820332.7, dated May 2, 2012 in 12 pages.
Sul YT, Johansson CB, Jeong Y, Wennerberg A, Albrektsson T. Resonance frequency and removal torque analysis of implants with turned and anodized surface oxides. Clinical Oral Implants Research, 13, 2002; 252-259.

* cited by examiner

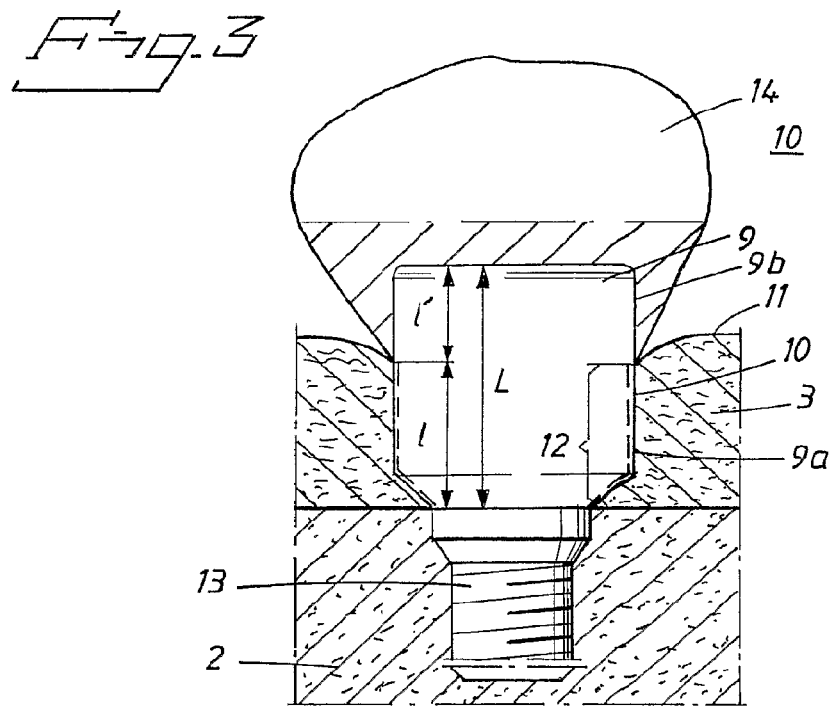
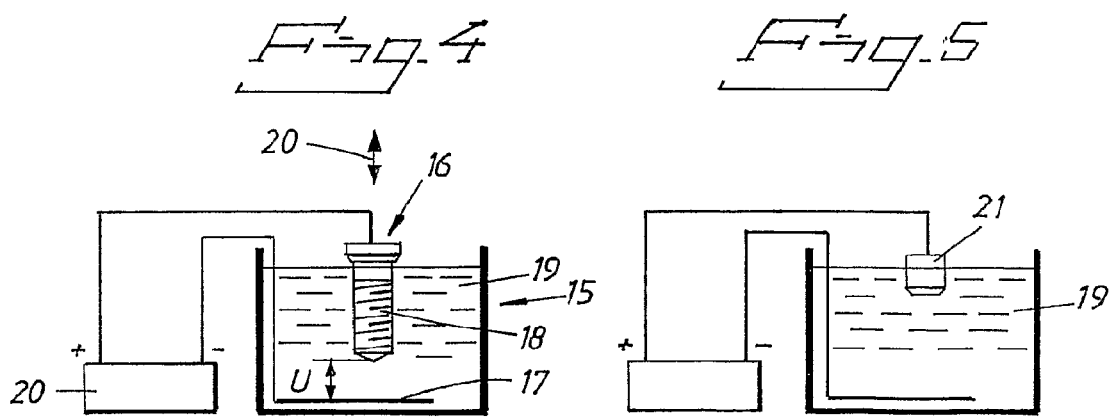
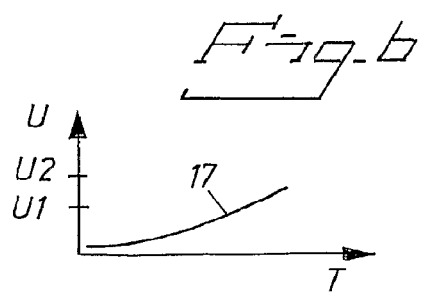

ARRANGEMENT WITH AN IMPLANT AND/OR A UNIT BELONGING TO SAID IMPLANT, AND METHOD FOR PRODUCTION OF THE IMPLANT AND/OR UNIT

This application is a divisional of U.S. patent application Ser. No. 10/582,468, filed Mar. 23, 2007, which is a U.S. National Phase of International Application No. PCT/SE2004/001806, filed Dec. 6, 2004, the entirety of which is incorporated by reference herein, and which claims the benefit of Swedish Application No. SE 0303323-0, filed Dec. 11, 2003.

The present invention relates to an arrangement with an implant and/or a unit, e.g. spacer sleeve, belonging to said implant, which are intended to extend through a hole formed in a jaw bone and through soft tissue of the jaw bone and to comprise one or more outer layers of titanium dioxide. The invention also relates to a method for production of the implant and/or unit.

Implants and spacer sleeves, or units passing through soft tissue, and methods for production of implants and such units in the dental field are already well known on the market and from descriptions in the patent literature and the general literature. Most of the known implants and units are designed in line with a general attempt to achieve good implantation results at reasonable costs. There is therefore a general need to obtain, between the implant and the jaw bone and between the part of the implant and/or unit extending through the soft tissue and the soft tissue, a good and also esthetically satisfactory integration which does not tend to degenerate after a period of implantation. The same Applicant as the one filing the present patent application has also submitted, inter alia, Swedish patent application 0301149-1, in which excellent integration was made possible between jaw bone and implant. Reference is also made to the patent applications filed at the same time as the present one, namely SE 03322-0 and SE 03324-8.

There is, however, a need for even better implants and units and for methods for production of implants and units. Thus, for example, it is important that bone growth can be improved and accelerated in connection with implants. There is an evident need for short fitting times, and it is more difficult for patients and dental personnel to accept long and protracted treatment periods. It is also important to achieve a good esthetic result in the long term, and also good integration of the upper parts of the implant or unit with respect to the jaw bone and soft tissue.

The object of the present invention is to solve these problems, inter alia, and it makes use of the knowledge that titanium dioxide can be arranged on the outer surface or outer surfaces of the implant. In a preferred embodiment, the application will be effected by means of so-called anodic oxidation, based on known methods according to Swedish patents 99019474-7 and 0001202-1. However, this known oxidation method has not been proposed to function in the crystalline range. Reference is also made to JP 2000116673 ad JP 11033106, Kokubo et al., relating to implant material which can be used in the crystalline range, but in principle outside the dental field.

The feature which can be regarded as characterizing an arrangement according to the invention is that each of the layers mentioned in the introduction will consist of crystalline titanium dioxide which largely or completely assumes the anatase phase.

In further developments of the inventive concept, the anatase phase is present in a proportion of 70-100% in one or more layers. The layers can also have a mean thickness in the thickness range of 0.05-10 μm, preferably 0.5-10 μm. In one embodiment, a large part or all of the outer surface or outer surfaces of the implant or of the unit is provided with the crystalline titanium oxide largely or completely assuming the anatase phase. In this way, the titanium dioxide layer according to the invention will stimulate excellent bone guidance and soft tissue integration. The crystalline titanium dioxide can be supplemented with another type of substance stimulating bone growth, e.g. BMP (bone morphogenetic protein). Further embodiments of the novel implant are set out in the attached dependent claims concerning the implant.

The feature which can principally be regarded as characterizing the novel method is that it comprises an anodic oxidation procedure. In this method, the part or parts bearing said outer layer or outer layers are applied to a liquid or electrolyte under voltage, e.g. sulphuric acid and phosphoric acid. The electrolyte composition and the voltage and the dwell time of the actual part or parts of the implant in the liquid are chosen so that titanium dioxide, largely or completely assuming the anatase phase, is formed. Different electrolyte compositions are associated with different voltages.

In one embodiment, the voltage is chosen with values between 100 and 270 volts. At lower voltages, the titanium dioxide layer becomes amorphous, and at higher voltages the quantity of rutile in the titanium dioxide layer increases.

By means of what has been proposed above, an excellent and effective bone growth function is obtained which is advantageous both from the point of view of strong growth of bone and from the point of view of time (rapid growth). The layer or layers also provide the possibility of effective soft tissue integration at the part or portion that can be placed against or extend through the soft tissue. The implant production is highly advantageous because methods and procedures already known per se can be used. No modifications are needed to the actual implant or unit structure, and they can be distributed and handled in the manner already practiced in the dental field. Likewise, the actual implantation work can follow already established routines, with the difference that bone growth, soft tissue integration and speed are increased. Layers with different properties can be positioned in all areas or selected areas of the implant, should this be desired.

BRIEF DESCRIPTION OF THE DRAWINGS

Presently proposed embodiments of an arrangement and of a method for production of the latter will be described below with reference to the attached drawings, in which:

FIG. 3 shows a vertical view of parts of an implant in a jaw bone (of which part is shown) and a through-piece belonging to the implant and extending through soft tissue, and portions of the unit that can be placed against the soft tissue have titanium dioxide layers in anatase phase, FIG. 4 shows a diagrammatic side view of titanium dioxide in the anatase phase being applied to an implant by means of anodic oxidation.

FIG. 5 shows a diagrammatic side view of titanium dioxide in the anatase phase being applied to a unit or soft tissue through-piece belonging to the implant, and FIG. 6 shows, in graph form, the layer thickness as a function of the applied voltage value.

DETAILED DESCRIPTION OF THE PREFERRED EMBODIMENTS

Figure 1:
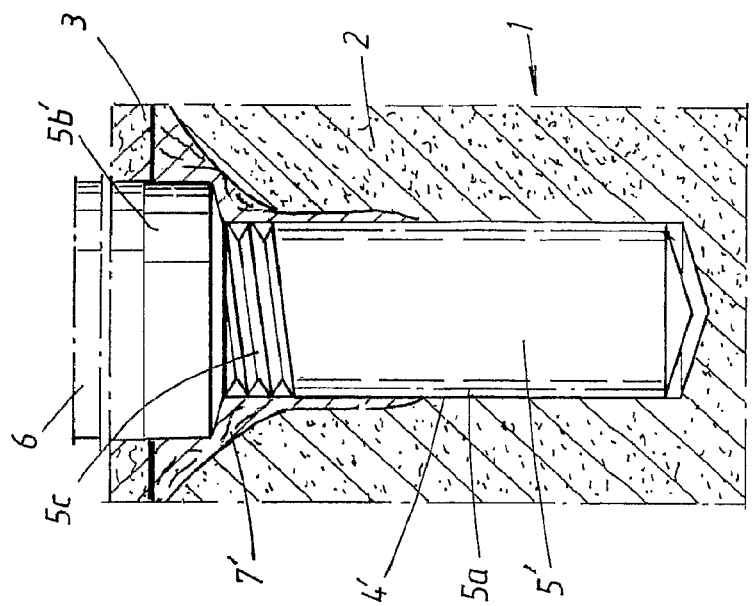
FIG. 1 shows a diagrammatic vertical view of an implant provided with a titanium dioxide layer in anatase phase and fitted in a jaw bone (of which part is shown), which layer, compared to the prior art, has an increased ability to guide bone formation.

According to FIG. 1, a bone 1 comprises jaw bone 2. On top of the jaw bone there is an area of soft tissue 3. The jaw bone is initially provided with a hole, shown symbolically by reference number 4. An implant 5 which can be of a type known per se is arranged in the hole. The implant can thus comprise, for example, an outer thread 5a by means of which said implant can be screwed into the hole 4. The hole can be threaded or unthreaded. The implant is also provided with an upper flange-like portion 5b which has a peripheral surface 5b' that can be placed against the jaw bone in the upper areas 2a thereof. The implant can also comprise or be connected to a unit or soft tissue through-piece 5, which can consist of or function as a spacer sleeve. On the soft tissue through-piece 5, the implant is intended to support a prosthesis, which is indicated symbolically by reference number 6. The surface of the jaw bone facing the portion 5b is indicated by 2a'.

The implant according to FIG. 1 is provided along all or most of its outer surface with a thin layer of titanium dioxide which completely or partially, preferably substantially, assumes the crystalline form anatase. Said anatase has been shown to have a powerful bone-growth-stimulating effect, which in FIG. 1 has been illustrated by bone growth 7 surrounding the implant along most of its length. The anatase layer has thus made the surface of the implant able to guide bone formation. The structure of the layer is described in more detail below. In the case according to FIG. 1, the titanium dioxide layer has not been applied to the upper parts of the implant, meaning that a small space with soft tissue is present between the portion and the jaw bone as a result of slight bone absorption. Said space 8, which is normally not desirable, has been shown for illustrative purposes.

Figure 2:
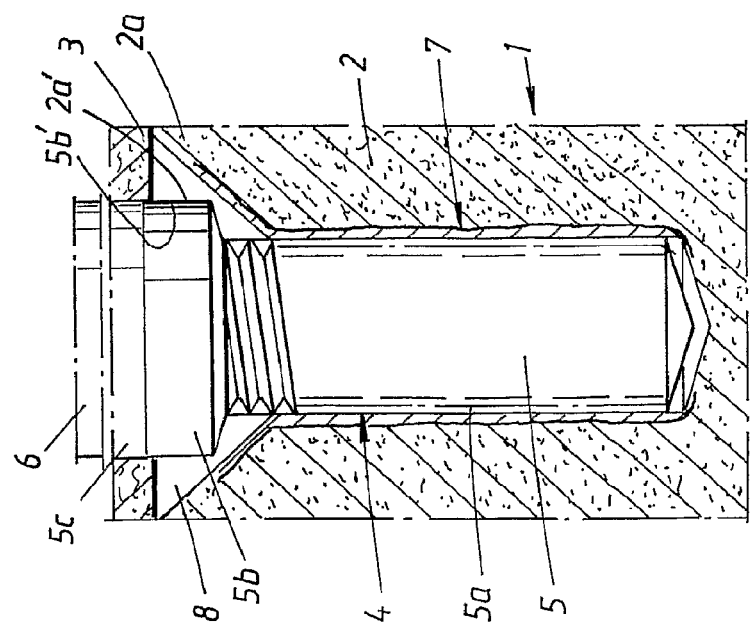
FIG. 2 shows a vertical view of an implantation case different than the one according to FIG. 1.

The implant according to the illustrative embodiment in FIG. 2 can have the same basic structure as the implant 5' in FIG. 1. In this case, the implant has titanium dioxide in the anatase phase only at its upper parts 5b' and 5c. The application of titanium dioxide in the anatase phase has brought about considerable bone growth 7' in the area concerned, cf. space 8 in FIG. 1. The titanium dioxide in the anatase phase can thus be used to effectively avoid bone absorption in the area according to the space 8 and in this way to avoid bone absorption and subsidence of soft tissue according to FIG. 1. This guarantees a good esthetic result even in the long term. Of course, the implant 5' according to FIG. 2 can be provided with titanium dioxide along the full outer extent of the implant. In this case, the hole formation has also been shown more clearly and is indicated by 4'. The arrangements shown in FIGS. 1 and 2 thus use the ability of the anatase layer to guide bone formation, which ability can be extended substantially compared to known dental techniques.

FIG. 3 shows a unit or through-piece 9 extending through the soft tissue 3. The unit 9 has a length L in the height direction. Along a length 1, which can be ⅔ of L, the unit has been provided, on its outer surface part 9a, with a thin anatase layer 10, i.e. with a titanium dioxide layer in the anatase phase. On the remaining part 9b, with length 1', of the outer surface, the unit has a thin titanium dioxide layer which can be amorphous, rutile or in the anatase phase. Said remaining outer surface part is directed towards the oral cavity, indicated symbolically by 10. In FIG. 3, reference number 11 also symbolically represents oral epithelium which has a limited extent along the surface of the spacer/unit/through-piece. The connective tissue area 12 extends across the greater part of the area or outer surface 9a, 9b and thus corresponds to the outer surface 9a along the extent 1. The through-piece 9 can be integrated with or applied in a known manner to the jaw bone implant 13 which in FIG. 3 is fitted in a hole formed in jaw bone 2 in the same way as in the illustrative embodiment according to FIGS. 1 and 2. The through-piece is also arranged here to support a prosthetic superstructure 14.

FIGS. 4 and 5 show the principle of anodic oxidation, in which use is made of a vessel 15 with liquid containing an electrolyte, e.g. sulfuric acid and phosphoric acid in accordance with the technique indicated in said patent publications. In an anode and cathode arrangement, the implant represents an anode 16, and a contact unit a cathode 17. The implant is designated by reference number 18 and is completely or partially immersed in the electrolyte 19. The anode and the cathode are connected respectively to the plus pole and minus pole of a voltage source which is symbolized by 20. The voltage source can comprise control members of a known type to ensure that the voltage between the anode/implant and the cathode/contact unit located in the electrolyte can be varied if necessary. Thus, the voltage U can, for a certain composition of the electrolyte, be varied or set to a first value in the range of 100-270 volts. If the electrolyte has another composition, the value is set to another value which can be in the stated range, i.e. between 100 and 270 volts, so as to obtain on the outer surface or outer surfaces in question a titanium dioxide layer according to the above, which assumes the crystalline anatase phase 7". The implant 18 can be acted on in the direction of the arrows 20, and it will be appreciated that the titanium dioxide layer can be varied in terms of thickness and phase by controlling the voltage value by means of said control members or setting members and by moving the implant in the directions of the arrows 20. The immersion time of the surface or surface parts is also crucial in determining the structure of the titanium dioxide layer.

FIG. 5 shows the case where a soft tissue through-piece or unit 1 is coated completely or partially with titanium dioxide in the anatase phase, using equipment according to FIG. 4. In the present example, lower parts (cf. 9a in FIG. 3) are immersed in the liquid bath or electrolyte 19. Otherwise, the arrangements according to FIGS. 4 and 5 function in a corresponding manner.

FIG. 6 shows how the thickness T can vary as a function of the voltage U for a certain immersion time and for a given electrolyte. The dependence of the layer thickness on, inter alia, the voltage has been represented by the curve 17. The graph also indicates a first voltage point U1 where the anatase phase occurs for the layer (cf. 7), while U2 indicates the voltage where the rutile phase occurs.

The thickness of the titanium dioxide layer can be chosen in the range of 0.05-10 μm, for example 0.5-10 μm. Anatase is present in a proportion of 70-100% in the layer in question. The implant and/or the soft tissue through-piece thus has a portion or portions that can be placed against the jaw bone and/or soft tissue. Each such portion can be unthreaded or can be provided with a thread, groove or pattern. Different layers can be provided on locally distinct sites or on top of one another.

To supplement the ability of the anatase to guide bone formation and to aid soft tissue integration, the titanium dioxide layer in anatase can be provided with growth-stimulating substance(s), e.g. BMP, which have bone-inducing properties.

The invention is not limited to the embodiment shown above by way of example, and instead it can be modified within the scope of the attached patent claims.

What is claimed is:

1. A method for producing one or more layers of titanium dioxide on a dental component, the dental component comprising a portion configured to oppose soft-tissue, the method comprising:
    exposing at least a portion of an outer surface of the portion configured to oppose soft-tissue to at least one of a liquid and electrolyte under voltage;
    selecting the voltage and dwell time such that at least one titanium dioxide layer is applied on the outer surface, wherein the titanium dioxide layer comprises crystalline titanium dioxide, the crystalline titanium dioxide being more in the anatase phase than any other phase of crystalline titanium dioxide.

2. The method of claim 1, wherein the titanium dioxide layer is between 70% to 100% anatase phase.

3. The method of claim 1, wherein the titanium dioxide layer has a thickness between 0.05 to 1.0 µm.

4. The method of claim 1, wherein the titanium dioxide layer has a thickness between 0.5 to 1.0 µm.

5. The method of claim 1, wherein the voltage is selected within the range of 100 to 270 volts.

6. The method of claim 1, wherein the outer surface extends two-thirds the length of the portion configured to oppose soft-tissue.

7. The method of claim 1, wherein the outer surface comprises the portions of the outer surface configured to contact connective tissue.

8. The method of claim 1, further comprising applying a layer of titanium dioxide having a different composition to a remaining part of the portion configured to oppose soft-tissue.

9. The method of claim 1, further comprising applying a bone stimulation substance to the titanium dioxide layers.

10. The method of claim 9, wherein the bone stimulation substance comprises BMP.

11. The method of claim 1, wherein the liquid comprises one of sulfuric acid and phosphoric acid.

12. The method of claim 1, wherein the portion configured to oppose soft-tissue is threadless.

13. The method of claim 1, wherein the portion configured to oppose soft-tissue is removable from the dental component.

14. The method of claim 1, wherein the titanium dioxide layer has a thickness between 0.05 to 0.25 µm.

* * * * *